United States Patent [19]

Tubesing et al.

[11] Patent Number: 5,013,763

[45] Date of Patent: May 7, 1991

[54] WASH-OFF-RESISTANT SKIN PREPARATION

[75] Inventors: David R. Tubesing, Erlanger; Maxine L. Truax, Fort Mitchell, both of Ky.

[73] Assignee: The Andrew Jergens Company, Cincinnati, Ohio

[21] Appl. No.: 126,453

[22] Filed: Nov. 30, 1987

[51] Int. Cl.⁵ ............................................. A61K 7/48
[52] U.S. Cl. .................... 514/772; 424/75; 424/81; 424/195.1; 514/782; 514/788
[58] Field of Search ............ 424/70, 78, 59, 65, 424/81; 514/772, 788, 782

[56] References Cited

U.S. PATENT DOCUMENTS

| | | | |
|---|---|---|---|
| 3,852,475 | 12/1988 | Tarangul | 424/361 |
| 4,054,670 | 10/1977 | Buhler | 424/358 |
| 4,137,302 | 1/1979 | Humbert et al. | 424/47 |
| 4,322,545 | 3/1982 | Scala | 560/103 |
| 4,323,694 | 4/1982 | Scala | 560/103 |
| 4,348,380 | 9/1982 | Jacquet et al. | 424/47 |
| 4,389,418 | 6/1983 | Burton | 424/365 |
| 4,438,095 | 3/1984 | Grollier et al. | 424/70 |
| 4,526,781 | 7/1985 | Goldberg et al. | 424/70 |
| 4,536,390 | 8/1985 | Padden | 424/47 |
| 4,559,225 | 12/1985 | Fourman | 424/59 |
| 4,563,346 | 1/1986 | Deckner | 424/59 |
| 4,590,069 | 5/1986 | Deckner et al. | 424/70 |
| 4,608,392 | 8/1986 | Jacquet et al. | 514/844 |
| 4,638,822 | 1/1987 | Grollier et al. | 132/7 |
| 4,673,525 | 6/1987 | Small et al. | 252/132 |
| 4,683,134 | 7/1987 | Palinczar | 424/59 |

FOREIGN PATENT DOCUMENTS 2076290 12/1981 United Kingdom .

OTHER PUBLICATIONS

*CTFA Cosmetic Ingredient Dictionary*, 2nd Edition N. F. Estrin, ed. (Cosmetic Toiletry and Fragrance Association Inc., Washington, D.C.) pp. 14, 18, 25, 54, 55, 57, 71, 96, 146, 227, 318).

Dow Corning, New Products Information, Jul. 8, 1970, pp. 1–7.

CTFA Cosmetic Ingredient Dictionary, 3rd Edition, N. F. Estrin, et al., ed. (Cosmetic, Toiletry and Fragrance Association, Inc.), pp. 94, 245, 267, 268.

"OTC Proposed Rule for Sunscreen Drug Products", Federal Register, No. 43, No. 166 (Aug. 25, 1978), p. 38267.

Amerchol Data Sheet on Polyquaternium-24 (Feb. 1987).

*Primary Examiner*—Amelia B. Yarbrough
*Attorney, Agent, or Firm*—Pennie & Edmonds

[57] ABSTRACT

A skin preparation such as skin lotion or cream which is resistant to being removed when the skin is washed includes a skin-preparation base and a plurality of wash-off-resistance substantivity agents. The wash-off-resistance substantivity agents include a polymeric skin-feel-modifying compound, a quanternary ammonium compound, a hydrophobic modified starch, a substantive silicone and a substantive emollient.

16 Claims, No Drawings

WASH-OFF-RESISTANT SKIN PREPARATION

TECHNICAL FIELD

The present invention concerns a skin preparation such as a hand lotion or body lotion for skin care or cosmetic applications.

BACKGROUND ART

Skin lotions are widely available for relieving dry skin and imparting a soft and smooth feel to the skin. However, conventional skin lotions readily wash off when the skin is washed with soap and water. Consequently each time after washing hands or bathing, a user must reapply the skin lotion to retain the benefits of the lotion.

Tarangul U.S. Pat. No. 3,852,475 discloses a composition for topical application which contains solid petrolatum and a hydrophobic starch such as an aluminum salt of a low substituted starch octenyl succinic half ester. According to the patent, the starch-containing petrolatum composition feels and appears less greasy when applied to the skin than conventional petrolatum jelly. In addition, the patent discloses that the combination of the hydrophobic starch and petrolatum is less resistant to washing with cold soap and detergent solutions than petrolatum alone.

Scala U.S. Pat. No. 4,323,694 is directed to certain benzoic acid esters useful in skin care compositions. Mineral oil, silicone oil, aluminum starch octenyl succinate and dimethicone are disclosed to be among many cosmetic ingredients which can be combined with the benzoic acid esters. Example 30 of the patent discloses an after-bath lemon body lotion which includes aluminum starch octenyl succinate.

Fourman U.S. Pat. No. 4,559,225 discloses a waterproof sunscreen composition which includes a film-forming cellulosic polymer, a solvent, an emollient, and a sunscreening agent. According to the patent, when spread on the skin, the composition leaves a non-greasy film with a superior resistance to removal by water. A preferred film-forming cellulosic polymer is disclosed at column 2, lines 21 through 27 to be a cellulose ether. Dimethicones are disclosed at column 2, lines 64 through 66 of the patent to be suitable plasticizers for the composition. An example of the sunscreen composition of the patent is set forth in column 3 and includes dimethicone and cellulose ethyl ether.

Small et al. U.S. Pat. No. 4,673,525 is directed to a skin cleansing composition. According to the patent, a polymeric ingredient sold under the tradename "Polymer JR" may be included in the cleansing compositions as a polymeric skin feel and mildness aid. See column 7, line 45 through column 8, line 2 of the patent.

British patent No. 2,076,290 to Mackles and Leone is directed to an antiperspirant stick composition. According to page 1, lines 13 through 15 of the patent, incorporating a starch into an antiperspirant stick along with other ingredients eliminates a greasy, oily feel. A suitable starch is disclosed to be the aluminum salt of the reaction product of octenyl succinate anhydride and starch, sold under the trade name of "DRY FLO." Silicone oils are also disclosed to be suitable for incorporation in antiperspirant sticks. Two examples of antiperspirant stick compositions on page 3 of the patent include "DRY FLO" starch and a silicone.

SUMMARY OF THE INVENTION

We have invented a skin preparation which is resistant to being removed when the skin is washed.

The skin preparation of the invention may be in lotion, cream, or other form. The skin preparation includes a skin-preparation base and a plurality of wash-off-resistance substantivity agents so that the skin preparation has a fraction of nonaqueous components retained as measured in a wash-off resistance test described below of about 70 percent or greater. The wash-off-resistance substantivity agents include a polymeric skin-feel-modifying compound, a quaternary ammonium compound, a hydrophobic modified starch, a substantive silicone and a substantive emollient. The terms "substantive" and "substantivity" refer in the present context to resistance to removal from the skin, consistent with the use of those terms in the cosmetic chemistry field.

Preferred skin-preparation bases for the skin preparation of the invention include mineral oil or petrolatum or both. Preferred skin-preparation bases may include in addition one or more of the compounds glycerin, urea, C12-15 alcohols benzoate, cetearyl alcohol, ceteareth-20, palm oil glyceride, isopropyl palmitate, cyclomethicone, 1-hexadecanol, stearyl alcohol, isopropyl myristate, sorbitol, POE sorbitan monostearate, avocado oil, glycerol dilaurate, and allantoin. Blends of cetearyl alcohol and ceteareth-20 are commercially available under the trade name "Promulgen D" from Amerchol Corporation of Edison, N.J., under the trade name "Cosmowax J" from Croda Corporation of New York, N.Y. and under the trade name "Lexemul CS-20" from Inolex Corporation of Philadelphia, Pa. Preferably the skin-preparation base is nonionic. An anionic skin-preparation base may interfere with the functioning of cationic ingredients in preferred skin preparations of the invention.

Preferred polymeric skin-feel-modifying compounds for the skin preparation of the invention include individually or in combination: (a) cationic cellulosic derivatives having a molecular weight in the range of from about 120,000 to about 850,000, such as a polymeric quaternary ammonium salt of hydroxyethyl cellulose reacted with a trimethyl ammonium substituted epoxide, more specifically, cellulose ω-ether modified with α-[2-hydroxy-3-trimethylammonio) propyl]-ω-hydroxy poly (oxy-1, 2-ethanediyl) chloride, also known under the trade designation polyquaternium 10; also useful are polyquaternium 4, 6, 7, 11, and 12; (b) guar gums; (c, nonionic polysaccharides such as nonionic hydroxypropyl guar gums—as an example, a nonionic hydroxypropyl guar gum commercially available under the trade name "Jaguar HP-60" from Hi-Tek Polymers, Inc. of Louisville, Ky.; (d) cellulosic nonionic polymers such as hydroxyethyl cellulose; (e) cationic starches such as, for example, 2-hydroxy-3-trimethyl ammonium chloride propyl ether of starch, commercially available under the trade name "Sta-Loc 300" and "Sta-Loc 400" from Staley, Inc. of Decateur, Ill., which has been reacted with quaternary amines to form ethers at a hydroxyl position; (f) copolymers of methacrylates and acrylamide, copolymers of dimethylaminoethylmethacrylate and acrylamide, and copolymers of dimethyldiallylammonium chloride and acrylamide- in the case of such copolymers the proportion of cationic monomer units to neutral monomer units is preferably selected to yield copolymers having a net cationic charge; (g) the polymeric compounds such as, for example, poly(dimethyl diallylammonium chloride) commercially available under the trade designation polyquaternium-6 or trade name "Merquat 100" and "Merquat 550" from Merck and . Inc. of Rahway, N.J. and related water-soluble cyclopolymers disclosed, for example, in Grollier and Allec U.S. Pat. No. 4,438,095 ("the Grollier and Allec '095 patent") at column 5, section 8; (h) the polymeric compounds such as, for example, guar hydroxypropyltrimonium chloride, commercially available under the trade name "Jaguar C-14-S" from Hi-Tek Polymers, Inc. noted above; (i) the polymeric compound commercially available under the trade designation polyquaternium-2 trade name "Mirapol A15"such as, for example, poly(oxy-1,2-ethanediyl) (dimethyliminio)-1,3-propanediyliminio carbonyl-imino-1,2-propanediyl(-dimethyliminio)-1,2-ethanediyl dichloride from Miranol Chemical Company, Inc. of Dayton N.J.; (j) the polymeric compound such as for example, hydroxypyl guar, commercially available under the trade name "Galactasol 811" from Henkel, Inc. of Teaneck, N.J.; (k) derivatives of cellulose ethers involving quaternary ammonium groupings, such as, for example, polymeric quaternary ammonium salt of hydroxylethyl cellulose reacted with trimethyl ammonium substituted epoxide commercially available from Union Carbide Corporation of Danbury, Conn., under the trade designations polyquaternium 10 or "JR" and "LR, " su as "JR-125," "JR-400,""JR-30M, ""LR-500" and a polymeric quaternary ammonium salt of hydroxyethylcellulose reacted with a lauryl dimethyl ammonium substituted epoxide "LR-30M," and under the trade designation polyquaternium-24 or trade name "Quatrisoft LM;" (l) derivatives of cationic cellulose such as, for example, diiallyldimonium chloride/hydroxyethylcellulose copolymer the polymers commercially available under the trade designation polyquaternium-4 trade names "Celquat L 200," "Celquat L 60," from National Starch Company of Bridgewater, N.J.; (m) homopolymers or copolymers of acrylic acid or methacrylic acid disclosed in the Grollier and Allec '095 patent at column 8, section 10; (n) polyalkylene imines such as, for example, polyethylenimines; (o) polymers containing vinylpyridine or vinylpyridinium units in the chain; (p) condensates of polyamines and of epichlorohydrine, quaternary polyureylenes, and chitine derivatives; (q) cationic proteins, such as steartrimonium hydrolyzed animal protein; and (r) nonionic proteins, such as collagen, hydrolyzed collagen, elastin, and hydrolyzed elastin. The concentration of the polymeric skin-feel-modifying compound in the skin preparation of the invention is preferably in the range of from about 0.05 to about 3 percent by weight relative to the weight of the skin preparation. More preferably, the concentration of the polymeric skin-feel-modifying compound is in the range of from about 0.1 to about 2 percent by weight.

Preferred quaternary ammonium compounds for the skin preparation of the invention include stearalkonium chloride, ditallow dimethyl ammonium chloride, distearyl dimethyl ammonium chloride, and cetyl trimethyl ammonium chloride. The concentration of the quaternary ammonium compound in the skin preparation of the invention is preferably in the range of from about 0.1 to about 6 percent by weight relative to the weight of the skin preparation, and more preferably in the range of from about 0.5 to about 4 percent by weight.

Preferred hydrophobic modified starches for the skin preparation of the invention include aluminum starch octenyl succinate and amylum non mucilaginosum starch. Preferred hydrophobic modified starches may be derived from a number of vegetable sources, including corn, wheat, potato, rice, waxy maize, sago, arrow root, tapioca, and sweet potato. The concentration of the hydrophobic modified starch in the skin preparation of the invention is preferably in the range of from about 0.5 to about 10 percent by weight relative to the weight of the skin preparation, and more preferably in the range of from about 1 to about 6 percent by weight.

Preferred substantive silicones for the skin preparation of the invention include dimethylpolysiloxane under the trade designation dimethicone or a modification of dimethicone such as amodimethicone or a mixture of dimethicone and trimethylsiloxy silicate. The concentration of the substantive silicone in the skin preparation of the invention is preferably in the range of from about 0.1 to about 8 percent by weight relative to the weight of the skin preparation, and more preferably in the range of from about 0.75 to about 4 percent by weight.

A substantive emollient is a substantive compound which tends to moisturize and protect the skin. Preferred substantive emollients for the skin preparation of the invention include 2-ethyl hexyl pelargonate, diisostearyl dimerate, isopropyl isostearate, isopropyl palmitate, and isostearyl neopentanoate. Diisostearyl dimerate is also referred to as diisostearyl dilinoleate. The concentration of the substantive emollient in the skin preparation of the invention is preferably in the range of from about 0.1 to 8 percent by weight relative to the weight of the skin preparation, and more preferably in the range of from about 0.5 to about 4 percent by weight.

All of the ingredients of the skin preparation of the invention should be safe for application to human skin in the preparation and their use should be approved by the applicable regulatory authorities as required.

If desired, the skin preparation of the invention may also include one or more moisturizers, stabilizers, humectants, sunscreens, preservatives, fragrances, or coloring agents.

A particularly preferred skin lotion of the invention includes five wash-off-resistance substantivity agents in a lotion base containing both petrolatum and mineral oil. The five wash-off-resistance substantivity agents are: (1) the polymeric skin-feel-modifying compound polyquaternium-10, a cationic cellulosic resin which is commercially available under the trade name "Polymer JR" from Union Carbide Corporation of Danbury, Conn.; (2) the quaternary ammonium compound distearyl dimethyl ammonium chloride; (3) the hydrophobic modified starch aluminum starch octenylsuccinate, which is the aluminum salt of the reaction product of octenylsuccinic anhydride with starch sold under the trade name "DRY FLO;" (4) the substantive silicones dimethicone and trimethylsiloxy silicate commercially available as a blend under the trade name "593 Fluid" from Dow Corning of Midland, Mich. or under the trade name "SS-4267" from General Electric Company of Waterford, N.Y.; and (5) the substantive emollient diisostearyl dimerate, which is the diester of isostearyl alcohol and dilinoleic acid. Four of the five wash-off-resistance substantivity agents individually when combined with a lotion base containing petrolatum and mineral oil improves the wash-off resistance of the resulting lotion to a degree as compared to the lotion base alone, as discussed below. However, when all five wash-off-resistance substantivity agents are combined with the same lotion base, the wash-off resistance is improved substantially relative to the lotion base combined with any of the individual ingredients alone or with any combination of two, three or four of the agents.

The preferred skin lotion described in the preceding paragraph including all five wash-off-resistant substantivity agents in a lotion base containing mineral oil and petrolatum was tested with consumers and found to leave the skin feeling moist, soft and smooth, even after the skin had been washed with soap and water subsequent to application of the skin lotion to the skin.

BEST MODE FOR CARRYING OUT THE INVENTION

Compositional formulas for six preferred skin lotions of the invention are set forth in Table I below. The skin lotions of Table I may be prepared by one of the two preferred methods set forth in the following paragraphs.

METHOD A

Into a jacketed mixing vessel is charged the required quantity of deionized water at about 25° C. Thereafter the required quantities of glycerin, allantoin, urea and polyquaternium 10 are added with mild agitation. The resulting mixture is slowly heated to between about 70° and about 75° C. with agitation for about 30 minutes. The resulting mixture is identified as component A.

In a separate jacketed mixing vessel is charged the required amounts of cetearyl alcohol and ceteareth-20, mineral oil petrolatum, palm oil glyceride, distearyl dimethyl ammonium chloride, dimethyl di(hydrogenated tallow) ammonium chloride (or quaternium-18, ditallowdimonium chloride or quaternium-48), isopropyl palmitate, C12-15 alcohols benzoate, 1-hexadecanol, stearyl alcohol, diisostearyl dilinoleate, isostearyl neopentanoate and aluminum starch octenylsuccinate. The resulting mixture is slowly heated with agitation to between about 70° and about 75° C. The resulting mixture is identified as component B.

Thereafter component B is added to component A with mild agitation. The resulting mixture is then cooled to about 45° C. and the remaining ingredients are added with moderate agitation until a homogeneous lotion is formed.

METHOD B

Method A is repeated with the exception that about 25 percent of the required deionized water is added to component B to improve its mixing properties.

WASH-OFF RESISTANCE TEST

A wash-off resistance test measures the ability of a lotion formulation to resist being washed off a surface by a solution of liquid detergent. A sheet of polyvinylchloride film approximately 0.002 inches (50 μm) thick was stored in a desiccator for about 24 hours to dry the film thoroughly. Polyvinylchloride film is a breathable material roughly similar to human skin. An embroidery hoop approximately six inches (150 mm) in diameter was placed on a laboratory scale and the scale tared to zero. A sheet of the dried polyvinylchloride film was stretched over the embroidery hoop to simulate a skin substrate. The embroidery hoop with the film mounted in it was then weighed to obtain the weight of the film. A sample of a lotion formulation of approximately one gram was spread generally evenly upon the polyvinylchloride film mounted in the embroidery hoop to form a thin layer. The embroidery hoop with the film and sample of lotion formulation was then promptly weighed to obtain the initial weight of the lotion formulation sample. The sample was then allowed to dry in air for approximately ten minutes.

An approximately one-percent solution by weight of detergent in water was prepared and placed in a laboratory beaker large enough in diameter to accommodate the embroidery hoop with roughly a one inch (25 mm) radial clearance about the perimeter of the hoop. A magnetic stirring bar was placed in the beaker and the beaker placed on a magnetic stirrer After the sample of lotion formulation on the polyvinylchloride film had dried for approximately ten minutes, a small weight was attached to the perimeter of the embroidery hoop holding the film and sample. The embroidery hoop was connected to a support bar placed across the top of the beaker at a point on the perimeter of the hoop generally diagonally opposite the weight, so that the hoop was suspended in the beaker with the weight at the bottom of the hoop. The weight caused the embroidery hoop to maintain a generally vertical orientation in the beaker. The embroidery hoop was restrained against rotating by the connection to the support bar. The detergent solution in the beaker was agitated mildly for about one hour by the magnetic stirrer with the embroidery hoop, the film, and the sample fully immersed in the solution. The solution of detergent was at a temperature in the range of from about 22° to about 25° C. The embroidery hoop film and sample were then removed from the detergent solution and the sample allowed to dry in air at approximately 50° C. for about 24 hours. The film of polyvinylchloride was then removed from the embroidery hoop and weighed to determine the weight of the residual sample left on the film after immersion in the agitated detergent solution. The result is reported as the fraction of the total sample retained in percent.

The initial ratio of the weight of the ingredients other than water to the weight of all ingredients including water can be calculated from the composition of the lotion formulation and reported as the fraction of nonaqueous ingredients in percent. The initial ratio of weight of nonaqueous ingredients to the weight of all ingredients is multiplied by the initial weight of the sample of lotion formulation to obtain the initial weight of nonaqueous ingredients in the sample. The resulting initial weight of nonaqueous ingredients is divided into the weight of the residual sample on the film after immersion and drying to obtain the fraction of nonaqueous ingredients retained, reported in percent.

A series of lotion formulations was prepared with a lotion base and various combinations of the following five wash-off-resistance substantivity agents in the weight percentages listed in column VI of Table I:

(1) dimethicone and trimethylsiloxy silicate,
(2) distearyl dimethyl ammonium chloride,
(3) aluminum starch octenyl succinate,
(4) polyquaternium 10, and
(5) diisostearyl dimerate.

Specifically, lotion formulations were prepared having the lotion base combined with every combination of from none to all of the five ingredients in the percentages given. When an ingredient was omitted from the formulation, an equal weight percentage of deionized water was substituted for it. The wash-off-resistance test described in the preceding paragraphs was carried out for each such lotion formulation to measure the fraction of total retained sample, the fraction of nonaqueous ingredients, and fraction of nonaqueous ingredients retained. The results of the tests are set forth in Table II below, in which the five wash-off-resistance substantivity agents are identified by number from the list above. In addition, the formulations of columns I through V of Table I and two commercially available hand lotions were tested by the wash-off-resistance test and the results are set forth in Table II. In the case of the two commercial hand lotions, the initial ratio of the weight of nonaqueous ingredients to the weight of all ingredients had to be estimated, since the exact composition of the lotions wa not known.

As may be seen in Table II, four of the five wash-off-resistance substantivity agents individually imparted a degree of wash-off resistance to the lotion base. The presence of all five wash-off resistance substantivity agents was found to give a fraction of nonaqueous ingredients retained of approximately 82.3 percent. As may be seen in Table II, any lotion formulation derived from column VI of Table I had a substantially lower average fraction of nonaqueous ingredients retained than the value observed for the base with all five ingredients. Moreover, each lotion formulation from Table I having all five wash-off-resistance substantivity agents had a substantially greater average fraction of nonaqueous ingredients retained than either of the commercially-available hand lotions tested.

It is not intended to limit the present invention to the specific embodiments disclosed above. It is recognized that changes may be made in the formulations specifically described herein without departing from the scope and teachings of the instant invention. For example, it is not necessary in every case to include all five classes of wash-off-resistance-substantivity agents in a preparation formulation to achieve substantial benefits of wash-off resistance and agreeable skin feel of the skin preparation of the invention, although inclusion of compounds from each of the five classes of agents in appropriate concentrations generally results in the best performance. It is intended to encompass all other embodiments, alternatives and modifications consistent with the present invention.

TABLE I

| Ingredient | I | II | III | IV | V | VI |
|---|---|---|---|---|---|---|
| | Approximate Weight Percent | | | | | |
| Mineral Oil | 2.0 | 1.0 | 4.0 | 1.0 | 3.0 | 1.0 |
| Petrolatum | 1.0 | 4.0 | 2.5 | 1.0 | 1.0 | 1.0 |
| Glycerin | 4.0 | 4.0 | 4.0 | 4.0 | 4.0 | 4.0 |
| C12-15 Alcohols Benzoate | 2.7 | 3.0 | 2.0 | 2.0 | 1.0 | 2.0 |
| Cetearyl Alcohol and Ceteareth-20 | 2.0 | 3.0 | 3.0 | 3.0 | 2.0 | 3.0 |
| Palm Oil Glyceride | 1.5 | 1.5 | 1.5 | 1.5 | 1.5 | 1.5 |
| Isopropyl Palmitate | 1.0 | 1.0 | 0.5 | 0.5 | 1.0 | 0.5 |
| 1-Hexadecanol | 0.5 | 0.5 | 0.5 | 0.5 | 0.5 | 0.5 |
| Stearyl Alcohol | 0.5 | 0.5 | 0.5 | 0.5 | 0.5 | 0.5 |
| Cyclomethicone | 0.5 | 1.0 | 1.5 | 1.0 | 0.5 | 1.0 |
| Allantoin | 0.2 | 0.2 | 0.2 | 0.4 | 0.1 | 0.2 |
| Urea | — | — | — | — | — | 3.0 |
| Polyquaternium-10 | 0.2 | 0.2 | 0.2 | 0.2 | 0.2 | 0.2 |
| Quaternium-18 | 1.0 | — | — | — | — | — |
| Quaternium-48 | — | 1.0 | — | — | 1.0 | — |
| Distearyl Dimethyl Ammonium Chloride | — | — | 1.0 | 1.0 | — | 1.0 |
| Aluminum Starch Octenylsuccinate | 1.5 | 5.0 | 4.0 | 3.0 | 3.0 | 3.0 |
| Dimethicone and Trimethylsiloxy Silicate | 3.0 | 2.5 | 3.0 | 2.5 | 2.5 | 2.5 |
| Diisostearyl Dilinoleate | 1.0 | — | 1.0 | 1.0 | 1.0 | 1.0 |
| Isostearyl Neopentanoate | — | 1.0 | — | — | 1.0 | — |
| Deionized Water, Perfume, Colorant, Preservative | (Balance to 100 percent) | | | | | |

TABLE II

| Composition | Fraction Total Retained (Percent) | Fraction Nonaqueous (Percent) | Fraction Nonaqueous Retained (Percent) |
|---|---|---|---|
| Base | 3.0 | 19.5 | 15.4 |
| Base + 1 | 6.0 | 22.0 | 27.2 |
| Base + 2 | 12.8 | 20.5 | 62.3 |
| Base + 3 | 5.0 | 22.5 | 22.2 |
| Base + 4 | 3.0 | 19.7 | 15.2 |
| Base + 5 | 14.0 | 20.5 | 68.2 |
| Base + 1 + 2 | 16.0 | 24.0 | 66.6 |
| Base + 1 + 3 | 6.0 | 25.0 | 24.0 |
| Base + 1 + 4 | 16.5 | 22.2 | 74.2 |
| Base + 1 + 5 | 9.5 | 24.0 | 39.5 |
| Base + 1 + 3 | 12.8 | 22.5 | 56.8 |
| Base + 2 + 4 | 11.5 | 20.7 | 55.4 |
| Base + 2 + 5 | 13.5 | 21.5 | 62.7 |
| Base + 3 + 4 | 16.5 | 22.7 | 72.6 |
| Base + 3 + 5 | 9.0 | 24.5 | 36.7 |
| Base + 4 + 5 | 13.5 | 19.7 | 68.4 |
| Base + 1 + 2 + 3 | 17.0 | 26.0 | 65.3 |
| Base + 1 + 2 + 4 | 11.5 | 23.2 | 49.5 |
| Base + 1 + 2 + 5 | 16.0 | 24.0 | 66.6 |
| Base + 1 + 3 + 4 | 17.5 | 25.2 | 69.3 |
| Base + 1 + 3 + 5 | 12.5 | 26.0 | 48.0 |
| Base + 1 + 4 + 5 | 14.0 | 24.2 | 57.8 |
| Base + 2 + 3 + 4 | 18.0 | 23.7 | 75.8 |
| Base + 2 + 3 + 5 | 14.0 | 24.5 | 57.0 |
| Base + 2 + 4 + 5 | 14.5 | 21.7 | 66.7 |
| Base + 3 + 4 + 5 | 13.5 | 24.7 | 54.6 |
| Base + 1 + 2 + 3 + 4 | 17.5 | 26.1 | 66.9 |
| Base + 1 + 2 + 3 + 5 | 18.8 | 29.4 | 63.7 |
| Base + 1 + 2 + 4 + 5 | 17.0 | 24.1 | 70.4 |
| Base + 1 + 3 + 4 + 5 | 11.5 | 26.1 | 44.0 |
| Base + 2 + 3 + 4 + 5 | 16.8 | 24.6 | 68.0 |
| Base + 1 + 2 + 3 + 4 + 5 (Formulation VI) | 24.4 | 29.6 | 82.3 |
| Formulation I | 20.5 | 24.0 | 85.3 |
| Formulation II | 23.0 | 30.8 | 74.6 |
| Formulation III | 29.5 | 30.5 | 96.7 |
| Formulation IV | 20.5 | 24.2 | 84.7 |
| Formulation V | 19.5 | 25.2 | 77.3 |
| Commercial Hand Lotion A | 15.5 | 24.2* | 64.1* |
| Commercial Hand Lotion B | 7.5 | 16.5* | 45.5* |

*Estimated.

What is claimed is:

1. A skin preparation comprising:
    (a) a skin preparation base; and
    (b) a plurality of wash-off-resistance substantivity agents, the wash-off-resistance substantivity agents being selected from the group consisting of:
        (b1) a polymeric skin-feel-modifying compound in an amount of from about 0.05 to about 3 percent by weight of the skin preparation;
        (b2) a quaternary ammonium compound in an amount of from about 0.1 to about 6 percent by weight of the skin preparation;
        (b3) a hydrophobic modified starch in an amount of from about 0.5 to about 10 percent by weight of the skin preparation;

(b4) a substantive silicone in an amount of from about 0.1 to about 8 percent by weight of the skin preparation; and (b5) a substantive emollient in an amount of from about 0.1 to about 8 percent by weight of the skin preparation;

the skin preparation having a fraction of retained nonaqueous components as measured by a wash-off-resistance test of about 70 percent or greater.

2. A skin preparation comprising:
   (a) a skin preparation base;
   (b) a polymeric skin-feel-modifying compound in an amount of from about 0.05 to about 3 percent by weight of the skin preparation;
   (c) a quaternary ammonium compound in an amount of from about 0.1 to about 6 percent by weight of the skin preparation;
   (d) a hydrophobic modified starch in an amount of from about 0.5 to about 10 percent by weight of the skin preparation;
   (e) a substantive silicone in an amount of from about 0.1 to about 8 percent by weight of the skin preparation; and
   (f) a substantive emollient in an amount of from about 0.1 to about 8 percent by weight of the skin preparation;
said components present in combination in an amount effective to resist wash-off by detergent after said preparation is applied to skin.

3. The skin preparation according to claim 2 in which the skin-preparation base includes a compound selected from the group consisting or petrolatum and mineral oil.

4. The skin preparation according to claim 3 in which the skin-preparation base is a lotion.

5. The skin preparation according to claim 3 in which the polymeric skin-feel-modifying compound is a cationic cellulosic derivative.

6. The skin preparation according to claim 5 in which the polymeric skin-feel-modifying compound is a polymeric quaternary ammonium salt of hydroxyethyl cellulose reacted with a trimethyl ammonium substituted epoxide.

7. The skin preparation according to claim 3 in which the quaternary ammonium compound is selected from the group consisting of stearalkonium chloride, ditallow dimethyl ammonium chloride, distearyl dimethyl ammonium chloride, and cetyl trimethyl ammonium chloride.

8. The skin preparation according to claim 3 in which the hydrophobic modified starch is selected from the group consisting of aluminum starch octenylsuccinate and amylum non mucilaginosum starch.

9. The skin preparation according to claim 3 in which the substantive silicone is selected from the group consisting of dimethicone, amodimethicone, and trimethylsiloxy silicate.

10. The skin preparation according to claim 3 in which the substantive emollient is selected from the group consisting of 2-ethyl hexyl pelargonate, diisostearyl dimerate, isopropyl isostearate, and isostearyl neopentanoate.

11. The skin preparation according to claim 1 in which:
the concentration of the polymeric skin-feel-modifying compound is in the range of from about 0.15 to about 2 percent by weight relative to the weight of the skin preparation,
the concentration of the quaternary ammonium compound is in the range of from about 0.5 to about 4 percent by weight relative to the weight of the skin preparation,
the concentration of the hydrophobic modified starch is in the range of from about 1 to about 6 percent by weight relative to the weight of the skin preparation,
the concentration of the substantive silicone is in the range of from about 0.75 to about 4 percent by weight relative to the weight of the skin preparation, and
the concentration of the substantive emollient is in the range of from about 0.5 to about 4 percent by weight relative to the weight of the skin preparation.

12. The skin preparation according to claim 11 in which:
the polymeric skin-feel-modifying compound is a polymeric quaternary ammonium salt of hydroxyethyl cellulose reacted with a trimethyl ammonium substituted epoxide,
the quaternary ammonium compound is distearyl dimethyl ammonium chloride,
the hydrophobic modified starch is aluminum starch octenylsuccinate,
the substantive silicone is a mixture of dimethylpolysiloxane and trimethylsiloxy silicate, and
the substantive emollient is diisostearyl dimerate.

13. The skin preparation of claim 2 having a fraction of retained nonaqueous components as measured by a wash-off-resistance test of about 70 percent or greater.

14. The skin preparation according to claim 6 in which the polymeric skin-feel-modifying compound is cellulose-ω-ether with α-[2-hydroxy-3-(trimethylammonio) propyl]-ω-hydroxy poly (oxy-1, 2-ethanediyl) chloride.

15. A skin preparation comprising:
   (a) a skin preparation base; and
   (b) a plurality of wash-off-resistance substantivity agents, the wash-off-resistance substantivity agents being selected from the group consisting of:
      (b1) a polymeric skin-feel-modifying compound in an amount of from about 0.05 to about 3 percent by weight the skin preparation, such compound being selected from the group consisting of cationic cellulose derivatives, guar gums, nonionic polysaccharides, cellulosic nonionic polymers, cationic starches, copolymers of methacrylate and acrylamide, poly(dimethyl diallyl ammonium chloride), guar hydroxypropyltrimonium chloride, poly(oxy-1,2-ethanediyl) (dimethyliminio)-1,3-propanediyliminio carbonylimino-1,3-propanediyl (dimethyliminio)-1,2-ethanediyl dichoride, hydroxypropyl guar, cellulose ether derivatives, homopolymers or copolymers of acrylic acid or methacrylic acid, polyalkylene imines, polymers containing vinylpyridine or vinylpyridinium units, condensates of polyamines and of epichlorohydrine, quaternary polyureylenes and chitin derivatives, cationic proteins, and nonionic proteins;
      (b2) a quaternary ammonium compound in an amount of from about 0.1 to about 6 percent by weight of the skin preparation, such compound being selected from the group consisting of stearalkonium chloride, ditallow dimethyl ammonium chloride, distearyl dimethyl ammonium chloride, and cetyl trimethyl ammonium chloride;

(b3) a hydrophobic modified starch in an amount of from about 0.5 to about 10 percent by weight of the skin preparation, such starch being selected from the group consisting of aluminum starch octenyl succinate, and amylum non mucilaginosum starch;

(b4) a substantive silicone in an amount of from about 0.1 to about 8 percent by weight of the skin preparation, such silicone being selected from the group consisting of dimethylpolysiloxane or modifications thereof and mixture of dimethylpolysiloxane and trimethylsiloxy silicate; and (b5) a substantive emollient in an amount of from about 0.1 to about 8 percent by weight of the skin preparation, such emollient being selected from the group consisting of 2-ethyl hexyl pelargonate, diisostearyl dimerate, isopropyl isostearate, isopropyl palmitate, and isostearyl neopentanoate;

the skin preparation having a fraction of retained nonaqueous components as measured by a wash-off-resistance test of about 70 percent or greater.

16. The skin preparation according to claim 15 in which:

the polymeric skin-feel-modifying compound is present in an amount of from about 0.15 to about 2 percent by weight of the skin preparation;

the quaternary ammonium compound is present in an amount of from about 0.5 to about 4 percent by weight of the skin preparation;

the hydrophobic modified starch is present in an amount of from about 1 to about 6 percent by weight of the skin preparation;

the substantive silicone is present in an amount of from about 0.75 to about 4 percent by weight of the skin preparation; and the substantive emollient is present in an amount of from about 0.5 to about 4 percent by weight of the skin preparation.

* * * * *

UNITED STATES PATENT AND TRADEMARK OFFICE
CERTIFICATE OF CORRECTION

PATENT NO. : 5,013,763

DATED : May 7, 1991

INVENTOR(S) : David R. Tubesing and Maxine L. Truax

It is certified that error appears in the above-identified patent and that said Letters Patent is hereby corrected as shown below: TITLE PAGE:

ABSTRACT, line 1, after "as" insert --a--.

line 6, "quanternary" should be --quaternary--.

Column 3, line 5, after "and" insert --Company--.

line 12, after "compound" insert --such as, for example, poly(oxy-1,2-ethanediyl)(dimethyliminio)-1,2-ethanediyl dichloride--.

line 14, after "nium-2" insert --or--.

lines 14-17, delete "such as, for example, poly(oxy-1,2-ethanediyl)(dimethyliminio)-1,2,-ethanediyl dichloride.

line 28, "su" should be --such--.

line 29, after "LR-500" insert --"LR-30M,"--.

lines 31-32, delete "LR-30M,".

UNITED STATES PATENT AND TRADEMARK OFFICE
CERTIFICATE OF CORRECTION

PATENT NO. : 5,013,763
DATED : May 7, 1991
INVENTOR(S) : David R. Tubesing and Maxine L. Truax It is certified that error appears in the above-identified patent and that said Letters Patent is hereby corrected as shown below:

line 38, after "Celquat L60," insert --and "Celquat H100--.

Column 5, line 33, delete ";" after "mineral" and before "petrolatum" insert --,--.

line 36, after "um-18" insert --)-- and after "chloride" insert --(--.

Column 7, line 14, "wa" should be --was--.

Column 8, line 27, "1" should be --2--.

Signed and Sealed this

Eighth Day of September, 1992

Attest:

DOUGLAS B. COMER

*Attesting Officer*   *Acting Commissioner of Patents and Trademarks*